(12) United States Patent
Björck et al.

(10) Patent No.: US 12,370,226 B2
(45) Date of Patent: *Jul. 29, 2025

(54) PREVOTELLA COPRI COMPOSITIONS

(71) Applicant: PROPREV AB, Helsingborg (SE)

(72) Inventors: Inger Björck, Billinge (SE); Anne Nilsson, Rydebäck (SE); Fredrik Backhed, Kullavik (SE); Petia Kovatcheva-Datchary, Gothenburg (SE)

(73) Assignee: PROPREV AB, Helsingborg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/591,306

(22) Filed: Feb. 29, 2024

(65) Prior Publication Data

US 2024/0285695 A1 Aug. 29, 2024

Related U.S. Application Data

(62) Division of application No. 16/175,299, filed on Oct. 30, 2018, now abandoned, which is a division of application No. 14/895,132, filed as application No. PCT/SE2014/050650 on May 27, 2014, now Pat. No. 10,137,157.

(30) Foreign Application Priority Data

Jun. 3, 2013 (SE) .................................. 1350675-3

(51) Int. Cl.
| | | |
|---|---|---|
| A61K 35/74 | (2015.01) | |
| A21D 13/02 | (2006.01) | |
| A21D 13/40 | (2017.01) | |
| A23L 7/117 | (2016.01) | |
| A23L 33/135 | (2016.01) | |
| A23L 33/21 | (2016.01) | |

(52) U.S. Cl.
CPC .............. *A61K 35/74* (2013.01); *A21D 13/02* (2013.01); *A21D 13/40* (2017.01); *A23L 7/117* (2016.08); *A23L 33/135* (2016.08); *A23L 33/21* (2016.08); *A23V 2002/00* (2013.01)

(58) Field of Classification Search
CPC ....... A61K 35/74; A23L 7/117; A23L 33/135; A21D 13/40; A21D 31/02; A23V 2002/00
See application file for complete search history.

(56) References Cited

PUBLICATIONS

Hayashi et al. (International Journal of Systematic and Evolutionary Microbiology vol. 57, pp. 941-946).*

* cited by examiner

*Primary Examiner* — Robert A Zeman

(74) *Attorney, Agent, or Firm* — Stephen J. Weyer, Esq.; Stiles & Harbison, PLLC

(57) ABSTRACT

A product such as a food product, food ingredient, food supplement or medicament containing isolated *Prevotella copri* (*P. copri*). The food product, food ingredient and food supplement are suitable for ingestion and the medicament is suitable for use as a suppository or enema or enclosed in a capsule.

4 Claims, 11 Drawing Sheets

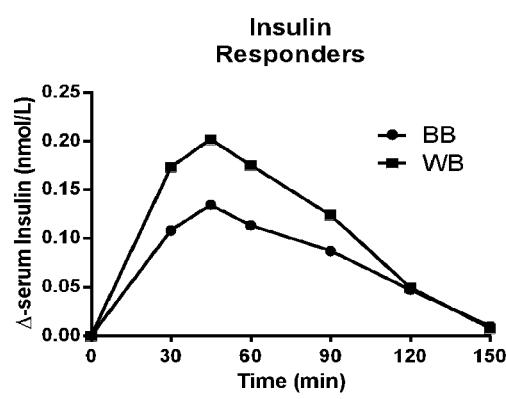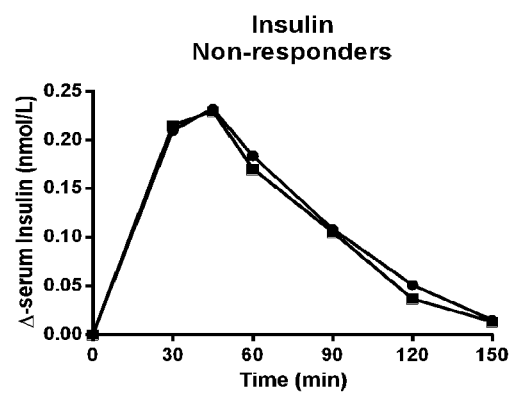
Fig. 6A                                    Fig. 6B

PREVOTELLA COPRI COMPOSITIONS

CROSS-REFERENCE TO RELATED APPLICATION

This application is a divisional of U.S. patent application Ser. No. 16/175,299 filed on Oct. 30, 2018, which is a divisional of U.S. patent application Ser. No. 14/895,132, filed Dec. 1, 2015, which is a U.S. national stage of PCT/SE2014/050650 filed on May 27, 2014, all herein incorporated by reference.

FIELD OF INVENTION

A product for use in the treatment of obesity, the metabolic syndrome, type 2 diabetes, cardiovascular diseases, dementia, Alzheimer's disease and inflammatory bowel disease comprising at least one isolated bacterial strain from the species Prevotellaceae, wherein the strain is selected from the group consisting of *Prevotella copri, Prevotella stercorea, Prevotella histicola, Prevotella ruminicola, Prevotella Bryantii* 25A and *Prevotella distasonis*. The product may be a food product.

BACKGROUND OF INVENTION

Many food—and ingredient companies within the field have increased their activities to identify ingredients as well as food products which upon use will provide beneficial health effects on the consumer in addition to providing essential nutrients, so called functional foods. Examples are viable microorganisms, so called probiotics which have shown specific health benefits on gut health and which are included in food product e.g. different dairy products such fermented milk, yoghurt, as well as different beverages. Other examples of food products with health benefits are foods containing dietary fiber (DF), prebiotic carbohydrates, stannol, omega-3 fatty acids, vitamins, polyphenols, low glycaemic impact foods etc.

From the public health perspective there is currently a particular need to develop new food products that could act to improve glucose metabolism and reduce obesity and related disorders. Impairment of glucose metabolism is also associated with impaired cognitive functioning. The prevalence of life style related disorders such as obesity and type 2 diabetes (T2D) is increasing globally, and it has been proposed that the number of people suffering from T2D worldwide will increase from presently 366 million to reach 552 million by year 2030. The need for preventive strategies is thus urgent. Diet based prevention is recognized as the most efficient strategy in the combat of life style related disease, and epidemiological studies support that e.g. high intake of whole grain foods and legumes is beneficial in the prevention and management of diabetes, and for weight control.

Obesity is a major factor contributing to cardio-metabolic disorders, but the underlying mechanisms are not fully known. However, a key feature appears to be "metabolic inflammation" and activation of the innate system. Dietary patterns for example high-GI food and energy dense food, are increasingly being considered predictive of future risk of cardiovascular diseases. Today, there is a growing body of knowledge in support of the importance of a healthy gut microbiota in the combat of cardiometabolic disorders and the gut eco-system is being acknowledged as modulator of host metabolism, appetite- and weight regulation. The metabolic "crosstalk" between the gut microbiota and peripheral tissues has been suggested to be regulated through gut fermentation of indigestible dietary components, such as indigestible carbohydrates.

Much of the evidence regarding the role of fermentable gut substrates on host metabolism stem from studies with inulin showing benefits on glucose metabolism and weight regulation in animal experimental models.

Recently the importance of the gut microbiota was documented in studies based on faecal transplantation from lean human donors to subjects suffering from the metabolic syndrome (MetS); the MetS representing a cluster of risk factors identifying subjects at high risk of developing T2D and cardiovascular disease. The faecal transplantation resulted in increased insulin sensitivity in the T2D subjects 6 weeks after faecal infusion. These new findings are exciting and add to the knowledge regarding the importance of a healthy microbiota. However, faecal transplantations may be both complicated and risky.

Thus there is a need for strategies to increase the number of beneficial bacteria, and promote a healthy balance of the gut microbial composition by other means. Up to date most studies demonstrating increases of beneficial bacteria following diet manipulation are cross sectional and thus do not demonstrate causality. This can be achieved by supplying viable bacteria through enemas, or through food products, including so called probiotics, or by dietary supply of sufficient amounts of colonic substrates e.g. specific prebiotic substrates in the habitual diet, or by combining pro- and prebiotics.

Despite the efforts in the food industry to develop new food products with improved health properties or functional food type products there is still huge problem with obesity as well as an increasing population of subjects with MetS or T2D. These conditions are typically treated with drugs. However, if healthy subjects or people at risk of disease could be offered food products specifically designed to counter-act early disease processes, this would prevent development of obesity and MetS, including impairment of cognitive functioning. Moreover, such food products could also facilitate disease management in patients with manifest disease related to MetS.

SUMMARY OF THE INVENTION

The invention relates to the unique finding that species belonging to Prevotellaceae have beneficial effects on host health. The species belonging to Prevotellaceae can be used in any kind of food products, or as an ingredient in a food product, as a probiotic with or without added indigestible carbohydrates, administrated enclosed in a capsule, as an enema or a suppository to improve the health of the consumer.

In a first aspect the invention relates to a product for use in the treatment of obesity, the metabolic syndrome, type 2 diabetes, cardiovascular diseases, dementia, Alzheimer's disease and inflammatory bowel disease comprising at least one isolated bacterial strain from the species Prevotellaceae, wherein the strain is selected from the group consisting of *Prevotella copri, Prevotella stercorea, Prevotella histicola, Prevotella ruminicola, Prevotella Bryantii* 25A and *Prevotella distasonis*. By such a product it is for the first time possible to provide new healthy food ingredients as well as food products, capsules, enemas or suppositories which could be useful in the treatment of a number of diseases mentioned above to improve glucose metabolism and reduce risk factors in the metabolic syndrome. The product may be provided together with one or more dietary fibers and/or resistant starch.

Further advantages and objects with the present invention will be described in more detail, inter alia with reference to the accompanying drawings.

BRIEF DESCRIPTION OF THE DRAWINGS

FIGS. 6A and 6B are graphs for serum insulin responses in responders (n=10) (FIG. 6A) and non-responders (n=10) (FIG. 6B) after the standardized breakfast, following 3 days consumption of barley kernel based bread (BB) and white wheat bread (WB), respectively. In the responders group, three days consumption of BB resulted in significantly lower insulin responses, compared to three days intake of WB (area under the curve 0-120 min, P<0.01). No improvements of the BB were seen in the non-responders group.

FIG. 8A and FIG. 8B are graphs that have six bars representing the groups involved in the study: R-control (responder control), R-WB (responders white wheat bread), R-BB (responders barley kernel based bread). NR=non responders. Control means that the samples have been collected without consumption of test breads (BB or WB).

DETAILED DESCRIPTION OF THE INVENTION

Definitions

Figure 1A:
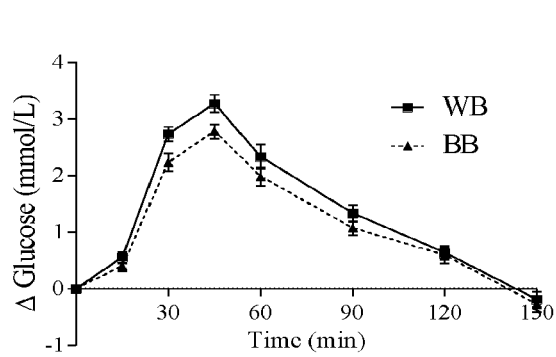
FIGS. 1A and 1B are graphs showing blood glucose (FIG. 1A) and serum insulin responses (FIG. 1B) (incremental changes (Δ)) to the standardized breakfast after 3 days consumption of barley kernel based bread (BB) and white wheat bread (WB), respectively. Consumption of BB resulted in lower postprandial glucose- and insulin peak concentrations (P<0.01, and P<0.001, respectively), and lower glucose- and insulin areas under the curves (0-150 min: P<0.01 and P<0.001, respectively) as compared to the reference WB (n=39).

In the context of the present application and invention, the following definitions apply:

The term "metabolic syndrome" or MetS is intended to mean the cluster of risk factors such as obesity, hyperlipidemia, hypertension and glucose intolerance, identifying subjects at high risk of developing type2 diabetes (T2D) and cardiovascular disease. The term "probiotic" is intended to mean a viable microorganism, such as bacteria that upon colonisation in the gut confer a health benefit on the host.

The term "dietary fibre" or "DF" is intended to mean carbohydrates including three or more monomers that resist digestion and absorption in the small intestine, and are completely or partially fermented in the colon by gut bacteria. In this application the term DF relates to non-starch derived indigestible polysaccharides such as beta-glucans, arabinoxylans, cellulose, oligosaccharides, fructans, pectin, guar gum. Indigestible substrates that are closely associated with indigestible polysaccharides in the plant are also included in the definition of DF (e.g., indigestible protein fractions, phenolic compounds, lignin, waxes, phytates, and phytosterols).

The term "resistant starch" (RS) is intended to mean starch- and starch degradation products that escape digestion in the small intestine of healthy individuals, i.e. starch derived DF. RS can deliver some of the benefits of insoluble DF and some of the benefits of soluble DF. RS may derive from botanically encapsulated starch, gelatinized—or retrograded starch.

The term "retrograded starch" is intended to mean re-crystallisation of starch molecules after cooking and cooling, resulting in structures resistant to digestion and absorption in the small intestine.

The term "botanically encapsulated starch" is intended to mean starch that is physically entrapped within the food matrix, or botanical cells making it inaccessible to digestive enzymes in the small intestine.

The term "gelatinized starch" is intended to mean unprocessed starch granules that occurs in its natural form, such as starch in uncooked potatoes or uncooked cereals, or starch granules that have resisted gelatinisation upon processing, resulting in a retained indigestible intact crystalline structure.

The term "prebiotic" is intended to mean indigestible food components, preferentially indigestible carbohydrates such as DF and RS, that stimulate the growth and/or activity of bacteria in the digestive system in ways associated with health benefits.

The term "synbiotics" is intended to mean a combination of probiotic and prebiotic.

The term SCFA is intended to mean short chain fatty acids produced from microbial gut fermentation of indigestible carbohydrates.

The term "encapsulated" is intended to mean that the *Prevotella* strain may be encapsulated to be protected from the environment (e.g. oxygen and acidity) and thus will be intact and retain the qualities and activities in the food product and during passage through the gut. The techniques used for encapsulation may be based on e.g. alginate-, guar gum-, xanthan gum-, locust bean gum-, carrageenan gum-, or other dietary fiber,-casein-, prebiotics—or starch based edible films, pickering emulsions etc. Different encapsulation technologies may be applied, which some are described by R Vidhyalakshmi et. al., 2009 [1].

The term "responders" is intended to mean human subjects that after consumption of the prebiotic barley kernel product received improved glucose regulation.

The term "non-responders" refers to human subjects that after consumption of the prebiotic barley kernel product do not display evidence of improved glucose regulation.

The term "enema" is used to depict a procedure by which a solution containing the *Prevotella* spp is introduced with or without prebiotic substrate to the gut through the rectum in order to beneficially modulate the gut microbial composition.

The term metabolic inflammation is used to depict: low-grade, chronic inflammation orchestrated by metabolic cells in response to excess nutrients and energy associated with insulin resistance and metabolic dysfunction.

*Segatella copri* is the new species name for the bacterium formerly known as *Prevotella copri* as discussed in the scientific article "A taxonomic note on the genus *Prevotella*: Description of four novel genera *Hallella* and *Xylanibacter*, by Hitch et al., published in Systematic and Applied Microbiology, 45 (2022) 126354. Therefore, *Prevotella copri* and *Segatella copri* are the same species.

The Invention

It has been found that intrinsic DF and RS in barley kernel products possess beneficial effects with respect to cardio-metabolic risk markers and appetite regulation, which is probably the same for other fibre groups as well. Hence, glucose tolerance and insulin economy was improved in a time perspective of 11-14 h after intake of barley kernel products, which is in an over-night perspective from a barley kernel evening meal to a subsequent standardised breakfast in healthy subjects.

Another important finding was an increase in plasma concentrations of GLP-1 and other appetite regulatory hormones, and a decrease in voluntary energy intake, while simultaneously reducing perceived hunger. In addition, barley indigestible carbohydrates reduced markers of metabolic inflammation. A state of increased metabolic inflammation is a recognized cardiometabolic risk factor, making food concepts that reduce metabolic inflammation promising in prevention of the MetS and T2D. Increased production of breath hydrogen (marker of gut fermentation) and SCFA were seen, indicative of increased gut fermentation activity after intake of barley indigestible carbohydrates. Significant associations were found between markers of gut fermentation and improved glucose regulation, demonstrating prebiotic mediated effects of barley kernel based products on metabolic risk markers, i.e. the beneficial effects seen are related to mechanisms derived from gut bacterial fermentation of indigestible carbohydrates. SCFA produced during gut microbiota fermentation provide energy to 40) colonic enterocytes, and in addition SCFAs also function as signaling molecules.

Consequently, it has been demonstrated that SCFA produced by bacterial fermentation may trigger signaling cascades through acting on SCFA receptors on L-cells, resulting in increased release of gut peptides such as GLP-1, and PYY (in vitro model). The results obtained clearly demonstrate a prebiotic potential of DF and RS in cereal products such as barley kernel products Surprisingly, it has been found in healthy subjects that the benefits observed after barley kernel products (bread) regarding cardio-metabolic risk markers and appetite regulation could be associated with a specific alteration of the gut microbiota, and we identified an increase in *Prevotella* species. Furthermore, the transfer of a specific *Prevotella* strain (*Prevotella copri*) to germ free mice improved glucose tolerance in the animals. The results put forward a probiotic effect of the identified bacterial strain with benefits on glucose metabolism. One of the criteria for selection of *Prevotella* strains was occurrence of glycoside hydrolases, needed for the degradation of complex sugars. All the selected strains have glycoside hydrolases, and are able to degrade a large range of complex sugars. An additional criterion was the selected strains to produce succinate as main products from the degradation of the complex sugars. Examples of the strains were *Prevotella copri*, *Prevotella stercorea*, *Prevotella histicola*, *Prevotella ruminicola*, *Prevotella Bryantii* 25A and *Prevotella distasonis*. Mixtures of one or more of the different strains may also be possible, such as 2, 3, 4, 5 or 6 different strains. The strain may be present in an amount of from $10^7$ or more such as $10^7$, $10^8$, $10^9$ or even to higher amounts.

In addition, the results for the first time reveal that the investigated prebiotic substrates. i.e. DF and RS present in barley kernel products, in combination with the *Prevotella* spp. strain could be particularly valuable in a synbiotic approach since these gut substrates favoured an increase in *Prevotella*. The results were obtained in middle aged/elderly healthy subjects at fasting and after a standardised breakfast after 3 days ingestion of a barley kernel based product (based on 100 g available carbohydrates/day). The barley kernel product was compared with a white wheat bread reference product using a cross-over design. By affecting the gut micro-biota composition and increasing the proportion of *Prevotella* spp, the barley kernel based product resulted in increased gut fermentation activity (breath hydrogen ($H_2$) as a test marker) ($P<0.001$), increased concentrations of SCFA ($P<0.05$), improved glucose regulation (reduced glucose- and insulin concentrations ($P<0.05$), increased concentrations of PYY (a satiety hormone released in the gut) ($P<0.05$), increased fasting concentrations of GLP-1 (an anti-obesity and anti-diabetic gut hormone), increased perceived fasting satiety, and reduced fasting hunger sensations. By altering the gut-microbiota composition and increasing the *Prevotella* spp, intake of barley kernel based food rich in barley DF and RS increased the gut fermentation metabolite succinate in both humans and mice.

The results further revealed that some individuals (approximately 15%) among the test subjects did not achieve an improved glucose regulation following intake of the barley kernel based test product (determined by glucose- and/or insulin response to a standardised meal after 3 days intervention with barley). Interestingly, neither did these "non-responders" acquire increased gut *Prevotella* concentrations after ingestion of the barley kernel product. This emphasise the causal relationship between the improved glycaemic regulation and increased abundance of *Prevotella* spp which is entirely new knowledge in the public domain. Also, these results indicate for the first time that certain individuals do not alter their gut microbiota composition as readily, and may particularly benefit from oral ingestion of the proposed combination of barley prebiotics (DF+RS) and *Prevotella* spp: or by *Prevotella* spp ingestion only.

By use of for example a barley kernel food product rich in DF and RS or DF or RS, benefits on blood glucose control, markers of metabolic inflammation, and appetite regulation have been established. The metabolic benefits were associated with markers of gut fermentation, i.e. breath hydrogen, plasma SCFA which indicates a prebiotics mechanism.

Gut microbial mapping of faecal samples from healthy humans ingesting the above mentioned barley kernel product revealed that the benefits on metabolic risk markers and appetite regulation were linked to a specific alteration of the composition of microorganisms present in the gut. Subjects that ingested the above mentioned barley kernel food product showed an increase in *Prevotella* species in the gut microbiota and improved cardiometabolic risk markers as compared to subjects that did not ingest the barley kernel food product (see the Examples below).

Further, it was shown that mono-colonisation of germ free mice with a *Prevotella* spp. strain improved glucose metabolism in the animals. Thus, the conclusion from the above results being that species related to *Prevotella* is suitable to be used as a probiotic with for example antidiabetic properties and weight regulating potential. The tight relation between impairment of glucose metabolism and impaired cognitive function also make relevant use of *Prevotella* species for prevention of cognitive decline associated with MetS. Other diseases or disorder are mentioned above.

From the above experiments and conclusion the invention was identified to be related to a product, such as a food product or food ingredient or formulation to be used as an enema, comprising at least one human isolated bacterial strain from the Prevotellaceae. The bacterial may be genetically modified, such as modified to produce succinate.

Examples are *Prevotella copri, Prevotella stercorea, Prevotella histicola, Prevotella ruminicola, Prevotella Bryantii* 25A and *Prevotella distasonis*.

The probiotic food product can be used alone, or in combination with other components, such as at least one type of dietary fibers, such as DF and RS or DF or RS and in some examples also succinic acid to regulate the glucose metabolism and reduce risk factors in the metabolic syndrome in a mammal such as in humans. Examples of diseases or disorders that would be treated includes treatment of obesity, the metabolic syndrome, type 2 diabetes, cardiovascular diseases, dementia. Alzheimer's disease and inflammatory bowel disease, such as obesity, metabolic syndrome and type 2 diabetes.

The probiotic food product may also comprise at least one DF and/or one RS, natural or synthetic, purified, mixtures or variants thereof. Examples of DF and RS are DF and RS from cereals or legumes such as viscous and non-viscous DF from barley, rye, wheat, oats, legume seeds, beta-glucans, guar gum, lignin, lignans and oligosaccharides such as galacto-oligosaccharides and fructo-oligosaccharides, botanically encapsulated RS, retrograded RS, chemically modified starch or ungelatinized RS. The product may comprise at least one type of resistant starch (RS), a natural one, synthetic, purified, mixtures or variants thereof. Examples of RS are vegetable starch such as retrograded starch, botanically encapsulated starch, ungelatinized starch and cyclodextrins, or chemically modified starch. The fiber may for example be from barley kernels. The ratio of RS/DF could for example be 10.8 (RS)/13.04 (DF). The DF could be dietary fiber from barley, wheat, rye, oats or extracted beta-glucans, guar gum, lignin, lignans and oligosaccharides such as galacto-oligosaccharides and fructo-oligosaccharides, botanically encapsulated RS, retrograded RS, chemically modified starch or ungelatinized RS. The product may comprise at least one type of resistant starch (RS), a natural one, synthetic, purified, mixtures or variants thereof. Examples of RS are vegetable starch such as retrograded starch, botanically encapsulated starch, ungelatinized starch and cyclodextrins, or chemically modified starch. The fibre may for example be from barley kernels.

The product may for example contain one or more bacterial strain together with RS and/or DS to achieve the expected results.

In another embodiment the invented product comprises an additional bacterial strain, wherein the said strain may produce succinate. Examples of such strains include any bacterial strain that is beneficial and includes e.g. *Lactobacillus*, such as *Lactobacillus reuteri, Lactobacillus rhamnosus, Lactobacillus acidophilus, Lactobacillus plantarum, Roseburia* and *Bifidobacteria*, such as *Bifidobacterium longum, Bifidobacterium lactis. Bifidobacterium animalis* and *Bifidobacterium bifidum*. The additional bacterial strain may as well be genetically modified, such as to produce succinate.

The product may also contain succinate in the free form or added with a succinate producing bacterial strain. A strain that produces succinate naturally or a strain that has been genetically modified to produce succinate.

Accordingly, the product may be capsulated or lyophilised which is well known for a person skilled in the art.

In another embodiment the bacterial strain from the Prevotellaceae is encapsulated in any form to protect the strain from oxygen. Examples of encapsulation techniques includes edible films, stable Pickering emulsions employing starch granules as barrier material, encapsulation based on polysaccharides e.g. beta-glucans, guar gum, xanthan gum, locust bean gum, carrageenan gum-, prebiotics, alginate, milk protein etc. Other techniques include inter-polymer complex formation in super-critical carbon dioxide. Different encapsulation technologies may be applied, which some are described by R Vidhyalakshmi et. al., 2009.

In another embodiment the bacterial strain/strains from Prevotellaceae can be provided through enema alone or in a composition with prebiotic substrates such as DF and/or RS.

The product may for example be any suitable food product and includes any food product that is not or mildly heat treated, or where the *Prevotella* can be introduced after heat-treatment, such as beverages, shots (e.g, fruit—or dairy based), smoothies, drinks, juices, table water, cold soups/soup mixes, oils products, spread, dressings, cold sauce/sauce mix, salsa, dairy products, ice-cream, and cereal based beverages, containing or supplemented with the *Prevotella* or the *Prevotella* and the prebiotic combined. The *Prevotella* may also be encapsulated and included in the foods described above, hence increasing resistance to environment and processing conditions.

The food product may also be heat-treated foods such as soft bread, crisp bread, flat-bread, tortillas, porridges, breakfast cereals, cereal bars or other snacks, potato powder or other instant food product, ready to eat meals, containing the prebiotic e.g, from barley, to be consumed with or without supplementation with the *Prevotella*. Capsules containing the *Prevotella* spp, to be ingested with the products listed above, or consumed for provision of the *Prevotella*. The capsules may additionally be made from prebiotic carbohydrates, e.g., from barley. The *Prevotella* may also be encapsulated e.g. by stable emulsion techniques and included in the foods.

The *Prevotella* spp, can also be provided as dry powder and packed in disposable containers to be added to meals, e.g, breakfast cereals. The food product can also be e.g. a drink, soup, yoghurt, cold cereal pudding or shot provided in a two chamber package, with *Prevotella* with or without prebiotic in one of the chambers and the food product as above in the other, to be mixed upon consumption. The chamber with *Prevotella* may also consist of a straw; which is included with the package, or distributed separately. The *Prevotella* will then be consumed by drinking through the straws.

The product can be a stable emulsion, where the *Prevotella* with or without prebiotics are encapsulated in emulsion droplets. These products can be administered as e.g, a shot.

In the case that the *Prevotella* are included in capsules, the capsules should preferably be in a form of entero capsules. *Prevotella* can also be included in entero tablets, depot tablets, depot (prolonged-release) capsules, or prolonged-release granules.

The product may also be a food ingredient that is to be added to a food product.

The invention also defines a product that could be used in the treatment of a number of diseases or disorders including those mentioned below. It could be used for the treatment of obesity, and associated disorders related to impaired blood glucose regulation such as type 2 diabetes as well as protection against subclinical inflammation and associated disease such as cardio-vascular disease. Additionally the protected concepts counteract features of the pathogenesis of dementia. Also, dysregulation of blood glucose is associated with inflammation and endothelial damage hence providing yet a link between the presently protected concept and prevention of cardiovascular disease.

Consequently, even mild impairment of glucose regulation in the normal range is related to a significantly lower performance in cognitive tests and the presently described concept improves gluco-regulation suggesting benefits adjunct to dementia. Also the presently described protected concept stimulate incretin hormones such as GLP-1. GLP-1 exert neuroprotective and anti-apoptotic effects, reduce beta-amyloid (Aβ) plaque accumulation, modulate long-term potentiation and synaptic plasticity, and promote differentiation of neuronal progenitor cells, hence preventing against dementia and Alzheimer's disease. The neuroprotective effects of GLP-1: possible treatments for cognitive deficits in individuals with mood disorders. Additionally the stimulation of GLP-2 observed with the protected concept protects against inflammatory bowel disease, and it is known that exogenous GLP-2 can protect the mucosa from chemotherapy-induced mucositis in rats.

The invention relates also to the identified product, such as a food product or food ingredient and the use of that product to improve glucose metabolism, lower metabolic inflammation, and facilitate appetite regulation as well as reduce risk factors in the metabolic syndrome. This could be useful in the prevention and regulation of disorder related to the MetS, such as obesity, glucose intolerance, diabetes or cardiovascular disease as well as in subject suffering from impairment of cognitive functioning related to the MetS. The invented probiotic may also be used in enema formulations or suppositories with or without prebiotic substrates.

The invention also relates to the use of the product as defined above to reduce risk factors in the metabolic syndrome, improve glucose metabolism, facilitate weight regulation and reduce risk of cognitive decline related to the MetS.

Finally, the invention relates to the use of succinate or a succinate producing bacterial strain to improve glucose metabolism, facilitate weight regulation and reduce risk factors in the metabolic syndrome.

The product may be used for humans, horses as well as dogs and cats.

Following examples are intended to illustrate, but not to limit the invention in any manner, shape, or form, either explicitly or implicitly.

EXAMPLES

Example 1

Prebiotic Carbohydrates in Barley Kernel Based Products Beneficially Affect Metabolic Risk Markers, Appetite Regulatory Hormones, and Perceived Satiety in Healthy Subjects Study Intension and Summary of the Study Design The aim of the study was to evaluate effects of intrinsic indigestible carbohydrates, DF and RS present in barley kernel based products on risk markers related to the MetS. Thirty-nine healthy middle-aged subject, aged $64.5\pm5.6$ years, with normal body mass indices (mean$\pm$SD=$23.6\pm2.3$ kg/m$^2$) were provided a barley kernel based bread—or a white wheat bread (WB, reference product) during three consecutive days in a cross-over design. The following day (day four) a standardised breakfast was served and physiological test markers determined at fasting and repeatedly in the postprandial period (0-180 min). The study was divided in three sub-studies (STUDIES A-C). The physiological test markers in STUDY A included determinations of blood glucose, serum insulin, breath hydrogen ($H_2$) excretion (marker of colonic fermentation), and registration of subjective appetite sensations. Venous blood was collected repeatedly for further evaluations in a sub-group of the cohort (see below). In addition, faecal samples were collected prior to start of the study and after each intervention period for characterisation of the gut microbiota (STUDY A).

From the cohort described above, additional physiological test markers were determined from 20 subjects, randomly chosen ($64.1\pm5.9$ years, $23.5\pm2.2$ kg/m$^2$) (STUDY B). In addition to blood glucose, serum insulin and breath $H_2$, also appetite regulatory hormones (PYY, GLP-1), and plasma short chain fatty acids (SCFA) were measured.

In STUDY C, 20 subjects from the cohort in STUDY A were chosen based on the degree of improvements in the glucose regulation at a standardized breakfast in an overnight perspective following ingestion of a barley kernel based product (BB) the previous evening. Included were the 10 subjects with most pronounced effects and the subjects with least pronounced effects of BB on glucose regulation. STUDY C is reported separately below.

Materials and Methods

Test Subjects

The inclusion criteria were age between 50-70 years, BMI normal to slightly overweight (BMI 18-28 kg/m$^2$), fasting plasma glucose value≤6.1 mmol/L, non-smoker, overall healthy, and no known metabolic disorders or food allergies. Anti-hypertensive medications and prescription-free pain-killers without any anti-inflammatory action were accepted. The studies were approved by the Regional Ethical Review Board in Lund, Sweden (Reference 2010/457).

STUDY A: Healthy volunteers, 6 men and 33 women aged 64.5±5.6 years, and with normal body mass indices (mean±SD=23.6±2.3 kg/m$^2$) participated in the study.

STUDY B: Twenty healthy volunteers, 3 men and 17 women, aged 64.1±5.9 years and with normal body mass indices (mean±SD 23.5±2.2 kg/m$^2$), were randomly chosen from the cohort in STUDY A.

Test Meals

The test meals were barley kernel based bread (BB) and white wheat bread (WB; reference meal). Each test product was consumed during three consecutive days, separated by two weeks. The quantity of the test and reference product, respectively, was calculated to provide 100 g of potentially available starch per day, analysed according to Holm et al. [2] (Table 1). For the two first days the daily intake was divided into three equal portion sizes to be consumed at approximately 0800, 1400 and 2100. On the third day, half of the daily intake (50 g available starch) was equally divided between the 0800- and 1400 meals, and the other half was consumed at 2100.

TABLE 1

Composition of the barley kernel bread (BB) and white wheat bread reference (WB) in STUDIES A-C.

| Products | Total starch | RS | Available starch[1] | Insoluble DF | Soluble DF | Total DF[2] | RS + DF |
|---|---|---|---|---|---|---|---|
| | % dry matter | | | | | | |
| WB | 77.4 | 1.92 | 75.5 | 3.55 | 1.38 | 4.93 | 6.85 |
| BB | 74.3 | 10.8 | 63.5 | 8.83 | 4.21 | 13.04 | 23.84 |
| | g/day | | | | | | |
| WB | 103 | 2.54 | 100 | 4.71 | 1.83 | 6.54 | 9.08 |
| BB | 117 | 17.0 | 100 | 13.97 | 6.64 | 20.61 | 37.61 |

[1]Calculated by difference; Total starch less RS (3-5).

[2]The DF mentioned in this application does not include physically inaccessible- or indigestible starch, i.e. RS.

Standardized Breakfast

A standardised breakfast was consumed after 3 days intervention with BB or WB, respectively, and consisted of 122.9 g WB corresponding to 50 g available carbohydrates, and 2.5 dl tap water.

Recipes and Preparation of Test Products

White Wheat bread (WB, reference meal and standardized breakfast); A WB was baked according to a standardized procedure in a home baking machine (Tefal home bread model nr. 573102; Menu choice, program 2 [white bread, 1000 g, quick (time2:32)]). The bread was made from 540 g of white wheat flour (Kungsörnen Ab, Järna, Sweden), 360 g water, 4.8 g dry yeast, 4.8 g NaCl (without Iodin). After cooling, the bread was sliced and wrapped in aluminium foil in portions sizes, put into plastic bags and stored in a freezer (−20° C.). The day before consumption the test persons were instructed to thaw the bread at ambient temperature, still wrapped in aluminium foil and in the plastic bag.

Barley kernel based bread (BB); A total of 595 g barley kernels was boiled in 520 g water for 12 min and was then cooled for 30 min in ambient room temperature. All water was absorbed into the kernels when cooked. Added to the kernels were 105 g wheat flour, 6 g dry yeast, 5 g salt, and 300 g water. The dough was kneaded for 4 min (Electrolux AKM 3000, N23 N25) and proofed for 30 min in a bowl, followed by another proofing (35 min) in a baking tin. The baking tin was covered with aluminium foil and baked in a household oven at 225° C. withholding a pan of water to maximize steam being present, until inner temperature of the bread reached 96° C. After baking the bread was cooled without the baking tin in wet towels in ambient room temperature. After cooling the bread was put in a plastic bag and left in room temperature during the night. The day after the breads were sliced and wrapped into aluminium foil in portion sizes, put into plastic bags and stored in a freezer (−20° C.)

Analysis of Total Starch, RS and DF in the Test Products

The test products were analysed with respect to total starch [3], RS [4], and DF [5]. Before analysis of total starch and DF, the breads were air dried and milled. RS in test products were analysed in products as eaten. Available starch was calculated by subtracting RS from total starch (Table 1).

Experimental Procedure

The study was a randomized (order of the test products) cross-over study, meaning that each subject participated in two three days interventions, consuming BB or WB, respectively, separated by approximately 2 weeks. The subjects were encouraged to standardize their habitual diet and meal pattern and to avoid alcohol, excessive physical exercise or food rich in DF during the days of consumption of the test or reference products. Furthermore, they should not have consumed antibiotics or probiotics during the previous 2 weeks and throughout the study. After the last test evening meal with barley kernel bread or WB, respectively, the subjects were fasting until a standardized breakfast was served the next morning. The subjects arrived to the experimental department at 0730, and an intravenous cannula (BD Venflon, Becton Dickinson) was inserted into an antecubital vein to be used for blood sampling. Fasting blood tests were collected, and satiety and breath $H_2$ registered before consuming the breakfast. The breakfast was consumed at ~0800 and within 13 min. In addition, measures of pre- and post-breakfast appetite were obtained using a 100 mm Visual Analogue Scale (VAS). During 2.5 h of repeated blood sampling, the subjects were told to maintain a constant and low degree of physical activity.

Sampling and Analysis of Physiological Variables and Breath Hydrogen in Expired Air Finger-prick capillary blood samples were taken for determination of blood glucose (HemoCue®B-glucose, HemoCue AB, Ängelholm, Sweden). Venous blood samples were collected to determine physiological test markers in serum (s) (s-insulin) and plasma (p) (p-SCFA, p-GLP-1, and p-PYY). Serum and plasma was separated by centrifugation and immediately stored in a freezer (−40° C.) until analyzed. Blood collecting tubes intended for analysis of plasma GLP-1, and PYY were prepared with an inhibition cocktail consisting of DPPIV (10 μl/ml blood) (Millipore, St Charles, USA) and Trasylol® 10 000 KIE/ml Aprotinin (50 μl/ml blood) (Bayer HealthCare AG, Leverkusen, Germany) prior to blood sampling. Tubes containing inhibition cocktail were kept on ice until usage, but maximum for 6 days. Commercial Kits based on enzyme-linked immunosorbent assays were used for determination of S-insulin (Mercodia, Uppsala, Sweden), PYY (3-36 and 1-36), and GLP-1 (active 7-36) (Alpco Diagnostics, Salem USA). SCFA (acetate, propionate, butyrate) were determined using a GC-method [6]. Breath hydrogen ($H_2$) in expired air was measured as an indicator of colonic fermentation activity using a Gastro+ (Bedfont EC60 Gastrolyzer, Rochester, England). Faecal samples were collected prior to the dietary intervention, and at day four, that is after three days consumption of test—and reference product, respectively. The subjects were instructed to collect faeces from the first defecation that occurred at day four and the sample was immediately frozen and handed over to the experimental department within 24 h for continued storage at −80° C., until analysis. A time schedule for determination of the physiological parameters is presented in Table 2.

TABLE 2

Time schedule for determination of test markers.

| | Time (minutes after start of the breakfast) | | | | | | | |
|---|---|---|---|---|---|---|---|---|
| | 0 | 15 | 30 | 45 | 60 | 90 | 120 | 150 |
| P-PYY | x | | | | x | | x | |
| SCFA | x | | | | x | | x | |
| P-GLP2 | x | | x | | x | x | | x |
| $H_2$ | x | x | x | x | x | x | x | x |

TABLE 2-continued

Time schedule for determination of test markers.

| | Time (minutes after start of the breakfast) | | | | | | | |
|---|---|---|---|---|---|---|---|---|
| | 0 | 15 | 30 | 45 | 60 | 90 | 120 | 150 |
| Glucose | x | x | x | x | x | x | x | x |
| P-GLP1 | x | | x | x | x | x | | x |
| S-insulin | x | | x | x | x | x | | x |
| Appetite sensations | x | x | x | x | x | x | x | x |

Calculations and Statistical Methods

GraphPad Prism (version 5, GraphPad Software, San Diego, CA, USA) was used for graph plotting. The incremental blood glucose- and serum insulin areas under the curves (iAUC, (concentrations as a function of time) were calculated for each subject and test meal, using the trapezoid model. Incremental peak (iPeak) concentrations were determined for glucose and insulin as individual maximum postprandial increase from baseline. Significant differences in test variables after the different test meals were assessed with ANOVA (general linear model), in MINITAB Statistical Software (release 16; Minitab, Minitab Inc, State College, PA). In the cases of unevenly distributed residuals (tested with Anderson-Darling and considered unevenly distributed when P<0.05), Box Cox transformation were performed on the data prior to the ANOVA. Correlations between parameters were performed using Pearson correlation in MINITAB Statistical Software (release 14; Minitab, Minitab Inc, State College, PA). Values of P<0.05 were considered significant. Data are expressed as means±SEM, values considered significant at P<0.05. Example 1: STUDY A: n=39, STUDY B: n=20, STUDY C: n=20.

Results

Study A (n=39)
Blood Glucose and Serum Insulin

Figure 1B:
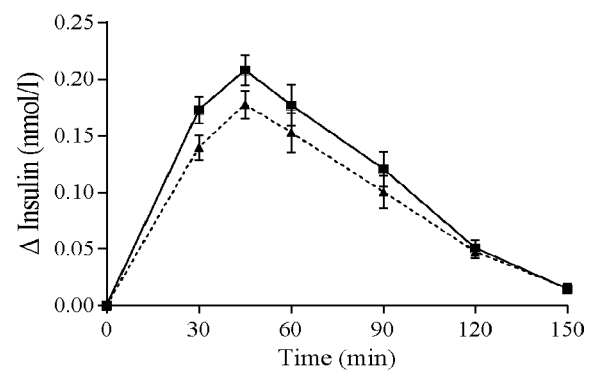

Three days consumption of BB significantly improved blood glucose response to the standardised breakfast in terms of postprandial peak concentrations (iPeak, P<0.01) and iAUC 0-150 min (P<0.01) as compared to the reference WB (Table 3). In addition, the BB resulted in significantly reduced insulin iAUC (0-150 min, P<0.001) and insulin iPeak (P<0.001, FIGS. 1A and 1B, Table 3).

TABLE 3

Blood glucose- and serum insulin responses to the standardized breakfast after 3 days consumption of barley kernel based bread (BB) or white wheat bread (WB), respectively.

| | Glucose (n = 39) | | Insulin (n = 39) | |
|---|---|---|---|---|
| | iPeak mmol/L | iAUC 0-150 min mmol · min/L | iPeak nmol/L | iAUC 0-150 min nmol · min/L |
| WB | 3.45 ± 0.14 | 215 ± 13.6 | 0.266 ± 0.019 | 16.2 ± 1.28 |
| BB | 2.99 ± 0.14** | 181 ± 11.7** | 0.230 ± 0.020*** | 13.7 ± 1.13*** |
| % Change | −13.4 | −15.8 | −13.6 | −15.5 |

*P < 0.05,
**P < 0.01,
***P < 0.001 (differences between WB and BB).

Breath $H_2$ Excretion

Consumption of the BB significantly increased breath $H_2$, as compared to the reference WB, indicative of increased gut fermentation activity after the BB (P<0.001. Table 4).

TABLE 4

Breath $H_2$ excretion and appetite sensations fasting and after the standardized breakfast, following 3 days consumption of barley kernel based bread (BB) or white wheat bread (WB), respectively.

| | $H_2$ | | Satiety | Hunger |
|---|---|---|---|---|
| | Fasting value N = 38 | Mean 0-150 min N = 39 | Fasting value N = 39 | Fasting value N = 39 |
| | Ppm | | mm | |
| WB | 11.39 ± 2.23 | 7.54 ± 1.04 | 31.44 ± 4.33 | 53.77 ± 3.51 |
| BB | 26.32 ± 3.42*** | 33.17 ± 4.26*** | 39.74 ± 4.26 * | 43.67 ± 4.52* |
| % Change | 131 | 339.92 | 26.4 | −18.78 |

*P < 0.05,
***P < 0.001 (differences between WB and BB)

Appetite Sensations

Three days consumption of BB resulted in increased satiety and reduced hunger at fasting the following day, compared with three days consumption of WB (P<0.05, Table 4).

STUDY A: SUMMARY AND CONCLUSIONS: Intake of a barley kernel based product resulted in improved postprandial glucose regulation at 11-14 hours post ingestion of the last portion. In addition the barley kernel based product increased satiety and reduced hunger sensation in the same time perspective. In parallel, breath hydrogen excretion increased, indicative of an increased colonic fermentation activity. The results suggest that the beneficial effects obtained after the barley kernel based product are mediated by increased gut fermentation, and activation of specific microbiota, of the intrinsic DF and RS, present in barley kernel based products.

Study B (additional test markers in n=20, randomly chosen from the cohort in STUDY A)

Blood Glucose and Serum Insulin Response

Figure 2A:
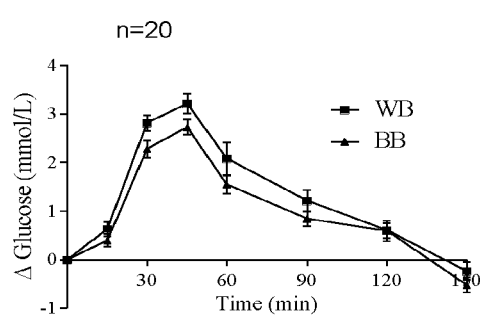
FIGS. 2A and 2B are graphs showing blood glucose (FIG. 2A) and serum insulin responses (FIG. 2B) (incremental changes (Δ)) to the standardized breakfast after 3 days consumption of barley kernel based bread (BB) and white wheat bread (WB), respectively. Consumption of BB resulted in lower postprandial glucose- and insulin peak concentrations (P<0.05 for both), and lower glucose- and insulin areas under the curves (0)-150 min: P<0.05 and P<0.01, respectively) as compared to the reference WB (n=20).
Figure 2B:
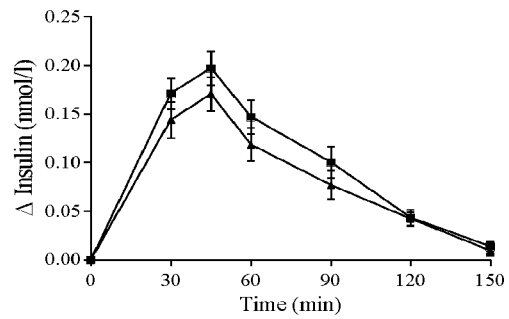

Three days consumption of BB beneficially affected the blood glucose response at the following standardized breakfast in terms of lower iPeak (P<0.05) and iAUC 0-150 min (P<0.05), as compared to three days consumption of WB. In addition, s-insulin iAUC (0-150 min) and insulin iPeak were significantly lowered (P<0.01 and P<0.05, respectively) (FIGS. 2A and 2B).

Markers of Gut Fermentation: Breath $H_2$ and SCFA

Figure 3:
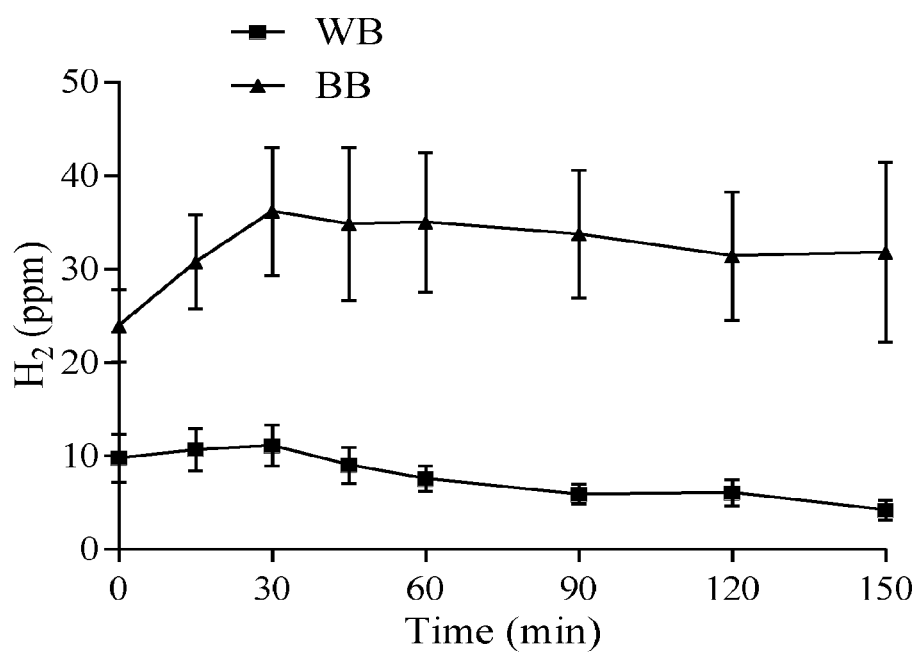
FIG. 3. Breath H2 excretion at the standardized breakfast, following 3 days consumption of barley kernel based bread (BB) and white wheat bread (WB), respectively. Consumption of BB resulted in significantly increased breath H2 compared to the reference meal WB (mean concentration during the experimental day, P<0.01 (n=20).

Three days consumption of BB resulted in significantly increased breath $H_2$ compared to the reference meal WB (P<0.01, FIG. 3, Table 5). In addition, intake of BB significantly increased the concentrations of s-acetate and concentration of total SCFA (P<0.05, Table 5). A non-significant increase of circulating s-butyrate was observed after BB compared to after WB (BB 16.1±0.7: WB 14.2±0.9; P=0.11). The results indicate an increased gut fermentation activity after the BB.

TABLE 5

Concentrations of SCFA in plasma at fasting, following 3 days consumption of barley kernel based bread (BB) or white wheat bread (WB), respectively.

| | Acetate Fasting value N = 19 μmol/L | Propionate Fasting value N = 19 μmol/L | Butyrate Fasting value N = 18 μmol/L | Total SCFA Fasting value N = 19 μmol/L |
|---|---|---|---|---|
| WB | 145.3 ± 11.5 | 9.84 ± 0.902 | 14.23 ± 0.864 | 170.2 ± 12.6 |
| BB | 171.5 ± 10.2* | 10.45 ± 0.793 | 16.01 ± 0.706[1] | 197.8 ± 10.3* |
| % Change | 18 | 6 | 13 | 16 |

*P < 0.05,
[1]P = 0.11

Gut-Related Hormones

GLP-1

GLP-1: is a hormone that is produced by the L-cells in the gut and that increases insulin secretion from the pancreas and increases insulin-sensitivity in both alpha cells and beta cells a glucose-dependent manner. GLP-1 also increases beta cells mass, inhibits acid secretion and gastric emptying in the stomach, and decreases food intake by increasing satiety in brain.

Consumption of BB test meals resulted in significantly increased concentrations of p-GLP-1 at fasting day four after BB (1.6±0.5 pmol/L) compared with after WB (1.0±0.4 pmol/L) (P=0.01).

GLP-2

The concentrations of p-GLP-2 were significantly increased during the experimental day after three days consumption of BB (mean 0-150 min: 3.5±0.5 ng/ml) compared to after WB (mean 0-150 min: 3.1±0.4 ng/ml, P<0.05).

PYY

PYY: is also produced by L-cells and inhibits gastric motility and has been shown to reduce appetite.

Figure 4:
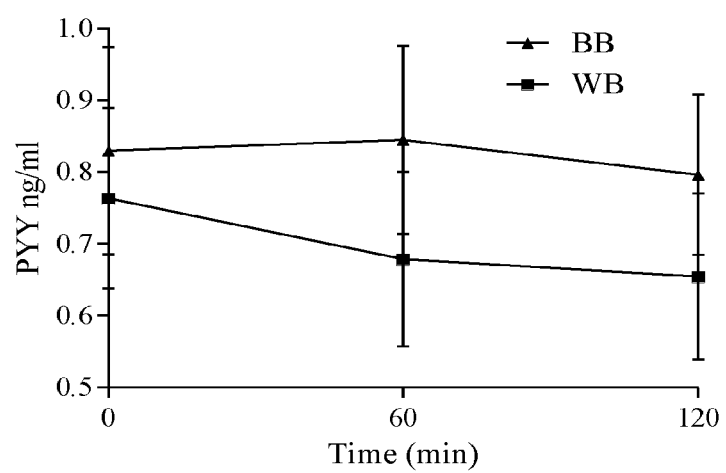
FIG. 4. Plasma PYY concentrations at the standardized breakfast, following 3 days consumption of barley kernel based bread (BB) and white wheat bread (WB), respectively. Consumption of BB resulted in significantly increased plasma concentrations of PYY (0)-120 min), compared to three days intake of WB (main effect during the experimental day. P<0.05 (n=20).

A significant main effect of test meals was observed revealing increased plasma concentrations of PYY (0-120 min) after three days consumption of BB, compared to three days intake of WB (P<0.05, FIG. 4).

Relationships Between Gut-Related Hormones and SCFA

After three days consumption of WB or BB, plasma concentrations of PYY correlated with plasma concentrations of total SCFA (r=0.51, P<0.05 and r=0.57, P=0.01) respectively.

STUDY B: SUMMARY AND CONCLUSIONS: The extended investigations show that, in addition to the results presented in STUDY A, the barley kernel based product increased plasma concentrations of gut hormones important to appetite- and glucose regulation in a time perspective of 11-14 hours after consumption. An increased gut fermentation activity was determined with increased breath hydrogen excretion and increased plasma concentrations of SCFA. In addition, the barley kernel product increased plasma concentrations of GLP-2, a gut hormone important to gut barrier functions by reducing the intestine wall permeability to e.g, endotoxins.

The study indicates that gut fermentation of intrinsic indigestible carbohydrates present in barley kernel based products may constitute a mechanism for a promising approach aiming at prevention and/or treatment of obesity and associated metabolic disorders STUDY C (n=20, chosen from the cohort in study a based on degree of improvements in the individual glucose regulation at the standardized breakfast.

Figure 5A:
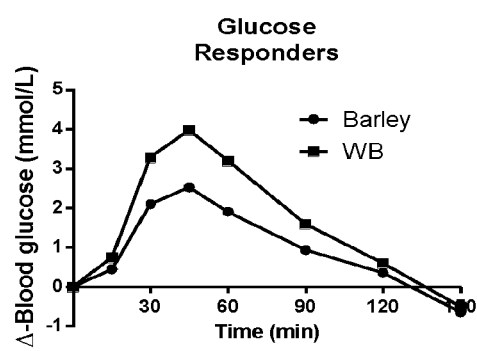
FIGS. 5A and 5B are graphs showing blood glucose responses in responders (n=10) (FIG. 5A) and non-responders (n=10) (FIG. 5B) after the standardized breakfast, following 3 days consumption of barley kernel based bread (BB) or white wheat bread (WB), respectively. In the responders group (FIG. 5A), three days consumption of BB resulted in significantly lower glucose responses, compared to three days intake of WB (area under the curve 0)-150 min, P<0.0001). No improvements in glucose tolerance (area under the curve) of the BB were seen in the non-responders group (FIG. 5B).
Figure 5B:
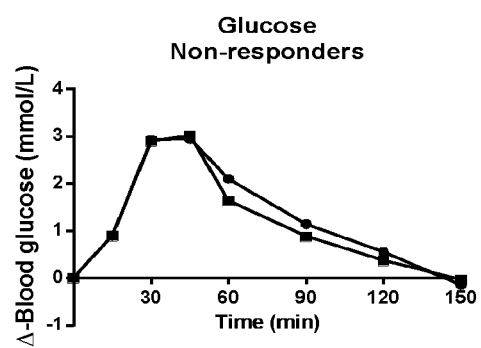

From the cohort in STUDY A (n=39, Example 1), 20 subjects (18 women and 2 men), aged (mean±SD) 64.9±5.1 years and with body mass indices (mean±SD) of 23.2±2.4 kg/m$^2$, were included in further investigations. The subjects were chosen with respect to the efficiency of the barley kernel product to improve the individual glucose regulation, in comparison to the WB. The 10 subjects (8 women and 2 men, 64.0±4.6 years, BMI 23.9±2.7 kg/m$^2$) in STUDY A with most pronounced effects of BB with respect to benefits on glucose regulation were included and denoted as "responders", and the 10 subjects (10 women, 65.7±5.3 years, BMI 22.5±1.7 kg/m$^2$) with least improvements in glucose regulation of BB were included and denoted "non-responders". The criteria used to define responders and non-responders are described below: In the responders group, three days consumption of BB resulted in significantly improved glucose tolerance (iAUC 0-150 min: 156±20) and 251±26 mmol*min/L after BB and WB, respectively, P<0.0001. FIGS. 5A and 5B) and decreased insulin response after the standardized breakfast (iAUC 0)-120 min: 10.3±1.5 and 15.3±2.1 nmol*min/L after BB and WB, respectively P<0.01. FIGS. 6A and 6B). In contrast, no significant improvements were seen on glucose tolerance (iAUC 0-150 min: 173±23 and 191±24 mmol*min/L after BB and WB, respectively. P=0.11) or insulin responses (iAUC 0)-120 min: 15.8±1.8 and 16.3±1.5 nmol*min/L after BB and WB, respectively. P=0.51) in the non-responders group.

Faecal samples collected prior to the study, and after consumption of BB and WB, respectively, were characterized with respect to the gut microbiota (see Examples 2).

Definition of "Responders" and "Non-Responders"

Responders were defined as those 10 subjects of the cohort in STUDY A (n=39) that achieved the most pronounced beneficial effect of the barley kernel product on glucose regulation. In responders the barley kernel product resulted in a decreased incremental blood glucose area (iAUC, 0)-90 min) after the standardized breakfast by at minimum 25% (between −25−(−67)%, mean=−39%), lowered total AUC in the same period of time, and decreased insulin iAUC after the standardized breakfast with at least 15% (−15−(−69)%, mean=−33%). Several of the remaining 29 subjects had either a lowered glucose response or a lowered insulin response. However, the 10 subjects with least improvements in glucose and/or insulin responses were denoted "non-responder". In the non-responders group (n=10), four subjects achieved no lowering of the glucose- and insulin responses after barley, three subjects had slightly lowered glucose responses, but no improvements in insulin responses, and three subjects achieved slightly lowered insulin response after BB, but no improvement in glucose responses.

STUDY C: SUMMARY AND CONCLUSIONS: The results show individual differences concerning the beneficial efficiency of barley kernels on glucose regulation in an 11-14 hours perspective. The reason for the individual discrepancies is suggested to be related to differences in the composition of the gut microflora.

A FOLLOW UP TO STUDY C was executed. The aim was to confirm the results previously obtained on glucose regulation and gut microflora following consumption of the BB versus the WB. The study design was similar to the design previously described. All subjects in study c (10 responders and 10 non-responders) were asked if they were willing to repeat the study. Seven responders (6 women and 1 man, 65.6±4.3 years, bmi 23.5±3.2 kg/m$^2$) and seven non-responders (7 women, 64.7±6.1 years, bmi 21.7±1.2 kg/m$^2$) accepted results.

Figure 7A:
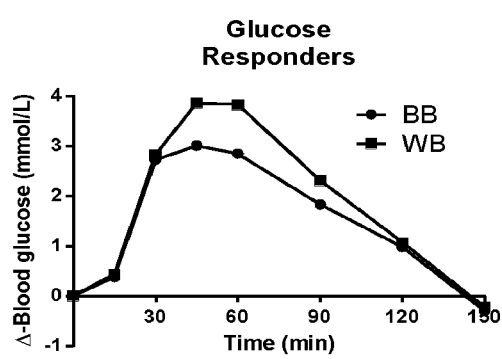
FIGS. 7A and 7B are graphs showing blood glucose responses in responders (n=7) (FIG. 7A) and non-responders (n=7) (FIG. 7B) after the standardized breakfast, following 3 days consumption of barley kernel based bread (BB) and white wheat bread (WB), respectively. In the responders group, three days consumption of BB resulted in significantly lower glucose responses, compared to three days intake of WB (area under the curve 0-150 min, P<0.0001). No improvements in glucose tolerance (area under the curve) of the BB were seen in the non-responders group.
Figure 7B:
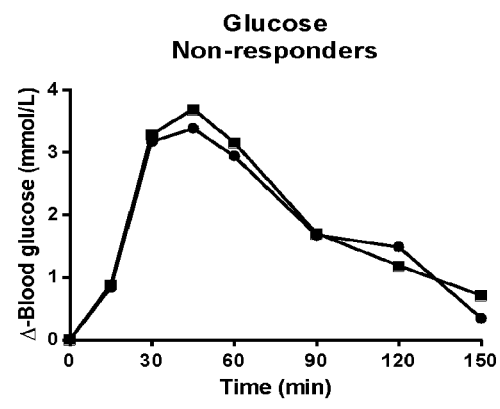

The results in the follow-up study were consistent with the previously obtained results. Consequently, in the responders group (n=7), the BB significantly improved glucose tolerance to the standardized breakfast (iAUC 0-150 min: 239±32 and 295±28 mmol*min/L after BB and WB, respectively, P<0.0001, FIGS. 7A and 7B), meanwhile no improvements of the BB were seen on glucose tolerance in the non-responders group (iAUC 0-150 min: 277±20 and 287±36 mmol*min/L after BB and WB, respectively, P=0.81).

SUMMARY AND CONCLUSIONS, TO FOLLOW UP STUDY: The results obtained in the follow-up study thus verifies the results obtained in the previous studies described above (studies A-C) concerning the beneficial effects on glucose regulation of DF and RS in BB, and indicates an individual component of the metabolic response.

Example 2

Characterization of Human Gut Microbiota Following Ingestion of WB or BB Products in Humans; and Inoculation Experiments in Mice for Validation of Causal Relationships Fecal DNA Extraction, Amplification, Pyrosequencing and Data Analysis.

Genomic DNA was isolated from 100-150 mg of feces per individual using the repeated bead beating (RBB) method previously described by Salonen et al [7]. Fecal DNA was quantified using a NanoDrop ND-1000 spectrophotometer (Nano-Drop Technologies) and the genomic DNA quality was assessed by gel electrophoresis using 1% Agarose-GelRed gel. An aliquot of the genomic DNA was diluted to 10 ng in 1 µl prior to use for PCR.

Amplification of the V1-V2 variable region of the 16 rRNA gene was performed using the 27F and 338R primers fused with 454 Titanium sequencing adapters to assess fecal microbiota diversity. 338R primers contained unique error-correcting 12-base barcodes that allow for multiple samples to be analyzed in a single sequencing run. Each sample was amplified in triplicate in a reaction volume of 25 μL containing 1.5 U of FastStart Taq DNA Polymerase (Roche), 0.2 μM of each primer and 1 μl (~10 ng) of the extracted genomic DNA. PCR was carried out under the following conditions: initial denaturation for 3 min at 95° C., followed by 25 cycles of denaturation for 20 sec at 95° C., annealing for 30 sec at 52° C., and elongation for 60 sec at 72° C., and a final elongation step for 10 min at 72° C. After PCR the triplicates were combined and the resulting product was checked for size and purity on 0.8% Agarose-GelRed gel. Then the samples were purified with the NucleoSpin Gel and PCR Clean-up kit (Macherey-Nagel. Germany) and quantified using the Quant-iT PicoGreen dsDNA kit (Invitrogen. Carlsbad. CA). Purified PCR products were diluted to a concentration of 20 ng in 1 μl and pooled in equal amounts. The pooled samples were then purified with the Ampure magnetic purification beads (Agencourt. Danvers. MA) to remove shorter amplification fragments. The pooled products were sequenced using the 454 GS FLX titanium chemistry at National Genomics Infrastructure (Stockholm).

Raw data were quality filtered to remove sequences that were shorter than 200 nucleotides, longer than 1.000 nucleotides, contained primer mismatches, ambiguous bases, uncorrectable barcodes, or homopolymer runs in excess of six bases. Quality filtered reads were trimmed from their 454 adapters and barcode sequences and were analysed with the software package Quantitative Insights Into Microbial Ecology (QIIME) (version 1.5.0). The number of reads that assed the quality filter totalled 755963 (mean 12599 sequences/sample). The sequencing data were denoised with denoise_wrapper.py a wrapper available in QIIME.

Sequences were assigned to operational taxonomic units (OTUs) using UCLUST with a 97% threshold of pairwise identity. The most abundant sequence was picked as representative for each OTU and was taxonomically assigned using the Ribosomal Database Project (RDP) Classifier. Representative OTUs were aligned using Pynast and used to build a phylogenetic tree with FastTree, which was used to estimate β-diversity of samples (weighted UniFrac).

Extraction and Quantification of Short Chain Fatty Acids.

120-190 mg of frozen faeces was transferred to a glass tube (16×125 mm) fitted with a screw cap and 100 μl of stock solution of internal standard ([1-$^{13}$C]acetate and [$^{2}$H$_{6}$] propionate at 1M concentration. [$^{13}$C$_{4}$]butyrate at 0.5M concentration. [1-$^{13}$C$_{1}$]isobutyrate and [1-$^{13}$C]isovalerate at 0.1M concentration. [1,2-$^{13}$C$_{2}$]hexanoate. [$^{13}$C]lactate and [$^{13}$C$_{4}$]succinic acid each in 40 mM concentration) was added. Prior to extraction the samples were freeze-dried at −50° C., for 3 h (yield 28-78 mg/dry weight). After acidification with 50 μl of 37% HCl, the organic acids were extracted (2 ml diethyl ether/extraction: 2 cycles). A 500-μl aliquot of the extracted sample was mixed together with 50 μl of N-tert-butyldimethylsilyl-N-methyltrifluoracetamide (MTBSTFA: Sigma) at room temperature. An aliquot (1 μl) of the resulting derivatized material was injected into a gas chromatograph (Agilent Technologies 7890 A) coupled to a mass spectrometer detector (Agilent Technologies 5975 C). A linear temperature gradient was used. The initial temperature of 65° C. was held for 6 min, increased to 260° C. (15° C./min) and further to 280° C., for 5 min. The injector and transfer line temperatures were 250° C. Quantitation was completed in selected ion monitoring acquisition mode by comparison to labeled internal standards (valerate was compared to [1-$^{13}$C]isovalerate, heptanoate and octanoate were compared to [1,2-$^{13}$C$_{2}$]hexanoate and fumarate was compared to [$^{13}$C$_{4}$]succinic acid). The m/z ratios of monitored ions were as follows: 117 (acetic acid), 131 (propionic acid), 145 (butyric acid), 146 (isovaleric acid), 159 (isovaleric acid and valeric acid, 173 (hexanoic acid), 187 (heptanoic acid), 201 (octanoic acid)), 261 (lactic acid), 287 (fumaric acid), 289 (succinic acid), 121 ([$^{2}$H$_{2}$]- and [1-$^{13}$C]acetate), 136 ([$^{2}$H$_{5}$]propionate), 146 ([1-$^{13}$C$_{1}$]isobutyrate), 149 ([$^{13}$C$_{4}$] butyrate), 160 ([1-$^{13}$C]isovalerate), 175 ([1,2-$^{13}$C$_{2}$]hexanoate), 264 ([$^{13}$C]lactate) and 293 ([$^{13}$C$_{4}$]succinic acid).

Results Regarding Faecal Microbial Pattern in Humans

Figure 8A:
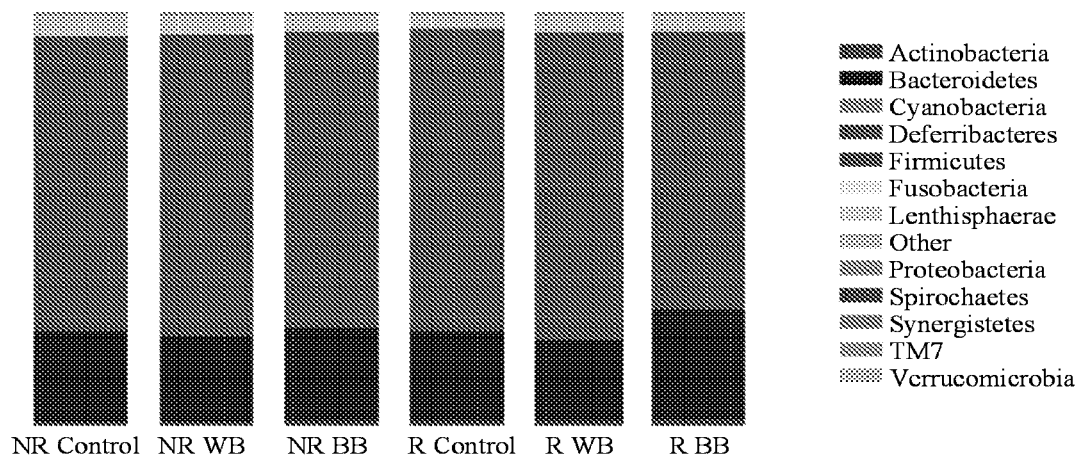
FIGS. 8A and 8B are graphs that show the taxonomic variation of the major gut microbial species across the different groups involved in the study, data has been generated after 454 pyrosequencing analysis.

Pyrosequencing of 16S rRNA gene barcoded amplicons resulted in 755 963 high-quality sequences, with a mean of 12599 sequences (range 7018-21116) per sample with similar amount of sequences generated in responders (R) and non-responders (NR) after each treatment. Firmicutes (~70%) was the most abundant phylum in each study group followed by Bacteroidetes (~20%). However, no significant differences in relative abundance of Firmicutes and Bacteroidetes were observed between responders or non-responders or by any treatment. A non-significant increase in the abundance of Bacteroidtetes was: however, noted in the Responder group on diet supplemented in barley kernel bread (FIG. 8A).

Figure 8B:
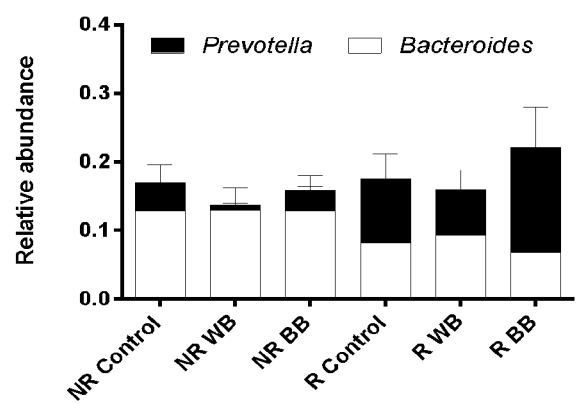

The Bacteroidetes phylum is composed by *Prevotella* and *Bacteroides* and interestingly we found significantly higher relative abundance in the responder groups of *Prevotella* (FIG. 8B, Two-way ANOVA, P<0.01). Furthermore, the levels of *Prevotella* increased after the barley kernel bread consumption in the responder group, which was not observed in the non-responders.

Moreover, significant increase in the faecal levels of succinate was measured in the responder group on diet supplemented in barley kernel bread (Table 6). Succinate is known to be the major metabolite from the fermentative activities of *Prevotella* species.

TABLE 6

Fecal concentration of organic acids.

| Metabolite umol/g dry weight | Responder Control | Responder WB | Responder BB | Nonresponder Control | Nonresponder WB | Nonresponder BB |
|---|---|---|---|---|---|---|
| Acetate | 92.82 | 93.47 | 77.58 | 90.95 | 100.92 | 79.51 |
| Propionate | 40.08 | 36.88 | 35.12 | 29.02 | 37.47 | 27.57 |
| Butyrate | 38.02 | 32.41 | 30.07 | 28.27 | 33.49 | 23.81 |
| Lactate | 3.54 | 12.86 | 5.37 | 4.73 | 4.89 | 8.30 |
| Succinate | 4.32 | 2.86 | 9.32 | 1.66 | 1.33 | 2.43 |

Innoculation Experiments in Mice

Ten- to twelve-week-old germ-free Swiss Webster male mice were inoculated with single gavage of 10$^{8}$ CFU Bacteroidetes *thetaiotaomicron* strain VPI-5482 (overnight culture in YCFA medium) or *Prevotela copri* strain DSM18205 (overnight culture in PYG medium) either in isolation or together. Both strains have been isolated from human faeces. Both were cultured and transported to the mice facilities in 15 ml Hungate tubes. Mono- and bi-colonized mice were housed in iso-cage system for 14 days. Prior sacrificing of the mice oral glucose tolerance test (OGTT) was performed. All mice were fasted 4 h prior OGTT. The colonization density was verified using qPCR assays that used species-specific primers. A control group of age-matched, gnotobiotic male Swiss Webster mice were also fed the same autoclaved chow diet ad libitum.

Mice were fasted for 4 hours and then given oral gavage of 60% D-glucose (3 g/kg body weight). Blood was drawn from the tail vein at 0, 30, 60, 90 and 120 minutes and blood glucose levels were measured using a HemoCue® glucometer. Extra blood was collected from the tail vein at 0, 15, and 30 minutes for analysis of serum insulin levels using insulin ELISA assay (Crystal Chem, Inc.).

Results

Figure 9A:
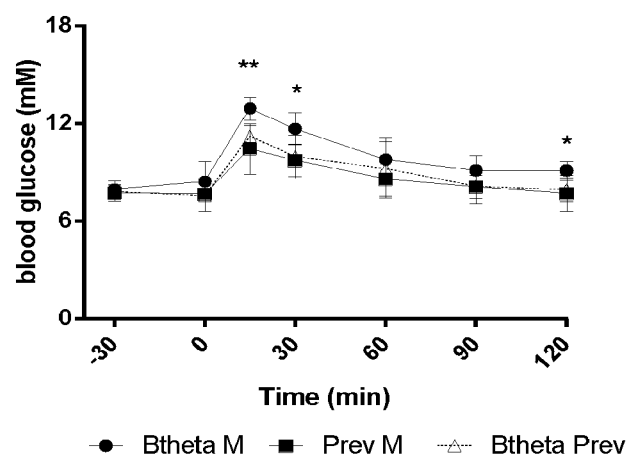
FIGS. 9A-9C are graphs showing that mice monocolonized with *Prevotella copri* (n=6) for two weeks exhibit improved oral glucose tolerance and lower serum insulin levels compared with mice mono-colonized with *Bacteroides thetaiotaomicron* (n=6) (P=0.0076). Mice bi-colonized with *P. copri* and *B. thetaiotaomicron* (n=7) also show better oral glucose tolerance in comparison with the mono *B. thetaiotaomicron* colonized mice (P=0.0426).
Figure 9B:
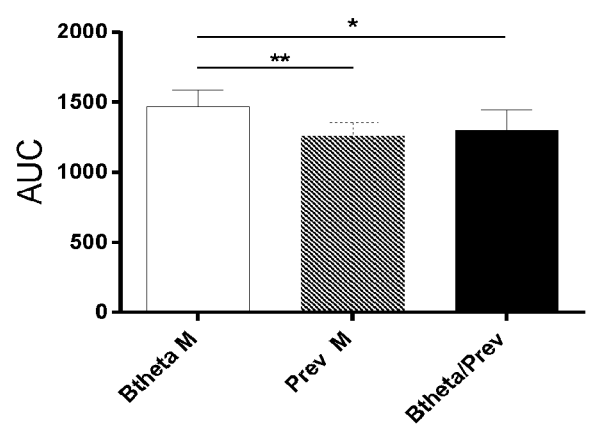
Figure 9C:
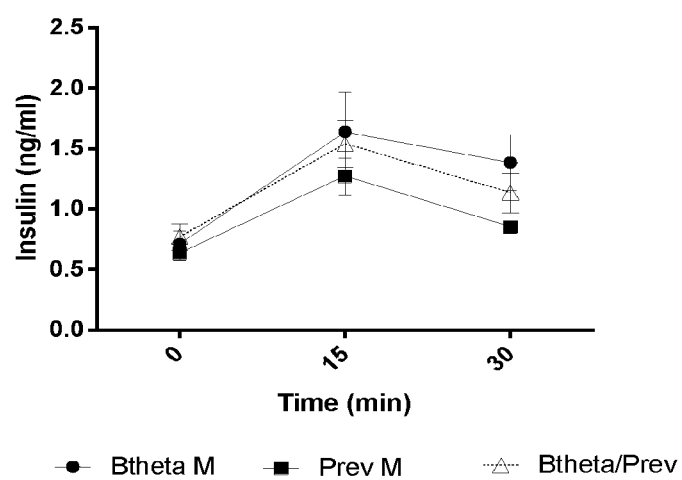

To investigate whether *Prevotella* has impact on improvements in glucose tolerance we mono colonized gnotobiotic mice with human feces-derived *Prevotella* strain—*Prevotella copri* and compared the glucose tolerance of those mice with mice mono colonized with *B. thetaiotaomicron* and bi-colonized with both strains. Colonization with *B. thetaiotamicron* caused impaired glucose tolerance compared with mice colonized with *P. copri* (FIGS. 9A-B). Additionally, the levels of serum insulin in the mice mono colonized with *P. copri* were lower at the 15 and 30 min after oral gavage of glucose, in comparison with the mice mono colonized with *B. thetaiotaomicron* (FIG. 9C). Importantly, *B. thetaiotaomicron* colonized mice exhibited improved glucose tolerance when they were co-colonized with *P. copri*. These data suggest that whereas *B. thetaiotaomicron* impairs glucose tolerance and that *P. copri* can prevent this impairment.

Example 3

Examples of Products

A) A beaker including one serving of yoghurt, with barley DF and/or RS and *Prevotella* ($10^7$ CFU or more), hermetically enclosed in the cap and separated by a membrane.
B) A bottle including one serving of drinking yoghurt, with barley DF, RS and *Prevotella* ($10^9$ CFU) hermetically enclosed in an accompanying drinking straw.
C) One serving of barley DF, RS, and *Prevotella* hermetically enclosed in single dose packages.
D) A bottle including one serving of fruit beverage, with barley DF and/or RS and *Prevotella* ($10^9$ CFU) hermetically enclosed in an accompanying drinking straw.
E) A bottle including one serving of fruit beverage, with barley DF and RS and *Prevotella* ($10^9$ CFU) hermetically enclosed in a cap and separated by a membrane.
F) An emulsified food product containing the encapsulated *Prevotella* in a matrix with or without the prebiotic carbohydrate component.
A-F) One portion of barley DF and RS and *Prevotella* (7 g insoluble barley DF, 3.3 g soluble barley DF, 8.5 g RS, and $10^9$ CFU *Prevotella*).

REFERENCES

1. Vidhyalakshmi, R., R. Bhakyaraj, and R. S. Subhasree, *Encapsulation "The Future of Probiotics"—A Review*. Advances in Biological Research 2009. 3(3-4): p. 96-103.
2. Holm, J., et al., *A rapid method for the analysis of starch*. Starch/Stärke, 1986. 38: p. 224-226.
3. Björck, I. M. E, and M. A. Siljeström, *In-vivo and in-vitro digestability of starch in autoclaved pea and potatoe products*. Journal of the Science of Food and Agriculture, 1992. 58: p. 541-553.
4. Åkerberg, A. K., et al., *An in vitro method, based on chewing, to predict resistant starch content in foods allows parallel determination of potentially available starch and dietary fiber*. The Journal of Nutrition, 1998. 128(3): p. 651-60.
5 Asp, N.-G., et al., *Rapid enzymatic assay of insoluble and soluble dietary fiber*. Journal of Agricultural and Food Chemistry, 1983. 31: p. 476-482.
6. Brighenti, F., *Summary of the conclusion of the working group on Profiber interlaboratory study on determination of short chain fatty acids in blood*, in Functional properties of non-digestible carbohydrates, F. Gullion, et al., Editors. 1998, European Comission, DG XII, Science, Research and Development: Brussels, Belgium, p. 150-153.
7. Salonen, A., et al., *Comparative analysis of fecal DNA extraction methods with phylogenetic microarray: effective recovery of bacterial and archaeal DNA using mechanical cell lysis*. J Microbiol Methods, 2010, 81(2): p. 127-34.

The invention claimed is:

1. A product selected from the group consisting of a food product, food ingredient, food supplement or medicament, said product comprising isolated *Prevotella copri* (*P. copri*), wherein the *P. copri* is encapsulated or lyophilized, or the *P. copri* is present in a capsule or formulated into one of a tablet, depot prolonged release capsule, prolonged release granules, and a powder.

2. The product of claim 1, wherein said *P. copri* is genetically modified.

3. The product of claim 1, further comprising succinate.

4. The product pf claim 1, wherein the food product is a probiotic food product.

\* \* \* \* \*